United States Patent [19]

Phillipps et al.

[11] Patent Number: 4,636,509
[45] Date of Patent: Jan. 13, 1987

[54] SUBSTITUTED PYRIMIDIN-2-ONES, THE SALTS THEREOF, PROCESSES FOR THEIR PREPARATION, PHARMACEUTICAL COMPOSITIONS CONTAINING THEM AND A METHOD THEREFOR

[75] Inventors: Gordon H. Phillipps, Wembley; Christopher Williamson, Cobham, both of United Kingdom

[73] Assignee: Glaxo Group Limited, England

[21] Appl. No.: 498,723

[22] Filed: May 27, 1983

Related U.S. Application Data

[63] Continuation of Ser. No. 283,645, Jul. 15, 1981, abandoned.

[30] Foreign Application Priority Data

Jul. 15, 1980 [GB] United Kingdom ............... 8023063

[51] Int. Cl.$^4$ ................. A61K 31/505; C07D 239/36
[52] U.S. Cl. ................................ 514/274; 544/316; 544/318
[58] Field of Search ............... 544/318, 316; 424/251; 514/274

[56] References Cited

U.S. PATENT DOCUMENTS 4,395,406  6/1983  Gacek et al. .................. 544/318
4,399,140  8/1983  Gacek et al. .................. 544/318

FOREIGN PATENT DOCUMENTS 2080300  2/1982  United Kingdom ............... 544/318
2080301  2/1982  United Kingdom ............... 544/318

Primary Examiner—Glennon H. Hollrah
Assistant Examiner—James H. Turnipseed
Attorney, Agent, or Firm—Bacon & Thomas

[57] ABSTRACT

Compounds of the general formula:

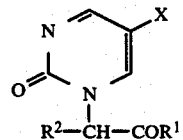

I (wherein X represents a halogen atom or a trifluoromethyl group; $R^1$ represents an optionally substituted $C_{6-10}$ carbocyclic aromatic group; and $R^2$ represents a hydrogen atom or a lower alkyl, $C_{7-16}$ aralkyl or $C_{6-10}$ aryl group or the group $COR^{1a}$, in which $R^{1a}$ is as defined for $R^1$, $R^1$ and $R^{1a}$ being the same or different) and where an acidic or basic group is present, the salts thereof have been found to possess excellent metaphase arresting ability and are of use in combating abnormal cell proliferation. Thus a knowledge of the cell division cycles of the normal and abnormal cells enables a cytotoxic drug to be administered while the abnormal cells are in a phase susceptible to attack and while the normal cells are in a non-susceptible phase.

The compounds of the invention are prepared by alkylation, deprotection of a protected keto group, oxidation or electrophilic halogenation.

Pharmaceutical compositions containing the compounds of formula I, and where appropriate, the physiologically compatible salts thereof; and methods for the use of the compounds are described and claimed.

12 Claims, No Drawings

SUBSTITUTED PYRIMIDIN-2-ONES, THE SALTS THEREOF, PROCESSES FOR THEIR PREPARATION, PHARMACEUTICAL COMPOSITIONS CONTAINING THEM AND A METHOD THEREFOR

This application is a continuation, of application Ser. No. 283,645, filed July 15, 1981, now abandoned.

The present invention relates to substituted pyrimidin-2-ones, the salts thereof, processes for their preparation, pharmaceutical compositions containing them and a method therefor.

Abnormal cell proliferation is present in a number of diseases such as cancers, leukaemias, cutaneous cellular proliferation, e.g. contact dermatitis or psoriasis, or auto-immune diseases where proliferation of lymphocytes leads to an undesirable immune response against some of the normal tissues of the body.

A number of drugs are known which combat abnormal cell proliferation by destroying the cells in one of the phases of cell-division in which they are particularly susceptible to such attack. In general, the cell-division cycle of both normal and abnormal cells includes a succession of phases, usually termed the G1, S, G2 and M phases, the last-mentioned being mitosis which in itself includes four well defined phases, prophase, metaphase, anaphase and telophase, related to the rearrangement of chromasomal material in the cell. In general, DNA synthesis takes place in the S phase, while protein synthesis takes place in the G1 and G2 phases. The S phase is usually significantly longer than the G1, G2 and mitotic phases.

However, the cells are not normally dividing synchronously and at the time of administration of a particular drug a random proportion of both normal and abnormal cells will be in a phase susceptible to attack. This means that the drug may be indiscriminate in its effects and if the treatment is at a dose level significantly effective against abnormal cells, a large number of body cells may also be irreversibly damaged.

The present invention is based, in part, on the concept of using a drug to arrest the cell-division cycle reversibly in a particular phase, namely the metaphase, so that during the period when an effective amount of the drug remains in the system, a large number of both normal and abnormal cells reach that phase and stop dividing. When the drug has been eliminated from the system, cell division is resumed by affected cells and is initially synchronous. However, the normal and abnormal cells usually divide at markedly different rates and, considering the cells affected by the drug, after a few hours the abnormal cells will be synchronously in one phase while the normal cells will be in another. It is then possible to administer a drug which is effective against cells in the phase reached by the abnormal cells but not effective against cells in the phase reached by the normal cells. Thus, for example, hydroxyurea and cytosine arabinoside are effective against cells in the S-phase, while vincristine and vinblastine are effective against cells in the mitotic phase.

We have found that the compounds of the invention as defined hereinafter are useful in combating abnormal cell proliferation. In particular they have excellent metaphase arresting ability.

According to one aspect of the present invention, therefore, we provide compounds of the general formula,

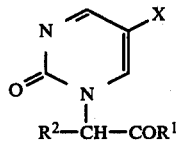

wherein
X represents a halogen atom, i.e. a fluorine, chlorine, bromine or iodine atom, or a trifluoromethyl group;
$R^1$ represents a $C_{6-10}$ carbocyclic aromatic group optionally substituted by one or more substituents selected from halogen atoms, hydroxyl, substituted hydroxyl, amino, substituted amino, $-S(O)_nR^a$ (in which n is 0, 1 or 2 and $R^a$ is lower alkyl), nitro, cyano, carboxyl, esterified carboxyl, carboxamido, $C_{1-4}$ alkyl, phenyl and methylenedioxy groups, which methylenedioxy group may carry alkyl substituents or, a perfluorinated alkyl group e.g. a trifluoromethyl group; and
$R^2$ represents a hydrogen atom or a lower alkyl, $C_{7-16}$ aralkyl or $C_{6-10}$ aryl group or the group $COR^{1a}$ (in which $R^{1a}$ is as defined for $R^1$, $R^1$ and $R^{1a}$ being the same or different); and, where an acidic or basic group is present, the salts thereof.

Certain compounds of formula I as hereinbefore defined and the salts thereof fall within the scope of the general disclosure in British Pat. No. 1,561,290, but there is no specific disclosure of any compound of the present invention. Moreover the compounds of the present invention possess especially good metaphase arresting ability compared with the compounds disclosed in British Pat. No. 1,561,290.

The term "alkyl" and "lower alkyl" as used herein in relation to a group or part of a group (i.e. moiety), unless otherwise stated, preferably relates to such groups or moieties containing from 1 to 6, especially 1 to 4, carbon atoms. The term "aryl" as used herein in relation to a group or part of a group (i.e. moiety) preferably relates to a phenyl group. Preferred aralkyl groups contain from 7 to 10 carbon atoms, e.g. benzyl. The term "substituted hydroxyl" as used herein includes alkoxy and aralkoxy, the alkyl and aralkyl moieties of which may be as defined above. The term "substituted amino" as used herein includes amino groups carrying either one or two alkyl, aralkyl or aryl groups as well as amino groups carrying either one or two acyl groups, for example, alkanoyl, haloalkanoyl or aroyl groups; as well as cyclic imido groups derived from dibasic alkanoic, aralkanoic or aroic acids.

Preferred compounds according to the present invention, by virtue of their especially favourable metaphase arresting ability, include compounds of formula I wherein $R^1$ represents a phenyl group optionally substituted by one or two substituents. Preferred substituents may be selected from halogen e.g. chlorine, bromine or fluorine atoms, and $C_{1-4}$ alkyl e.g. methyl, $C_{1-4}$ alkoxy e.g. methoxy, hydroxy, alkoxycarbonyl, nitro, trifluoromethyl, alkylthio, alkylsulphonyl, alkylsulphoxide, cyano and aroylamino. Such compounds of formula I are especially preferred in which $R^1$ represents an unsubstituted phenyl group or a phenyl group substituted by one or two substituents, selected from halogen e.g. fluorine, chlorine or bromine, hydroxy, cyano, aroylamino e.g. benzoylamino, alkoxycarbonyl e.g.

ethoxycarbonyl or methoxycarbonyl, alkoxy e.g. methoxy, alkyl e.g. methyl, nitro, alkylsulphinyl e.g. methylsulphinyl, alkylsulfonyl e.g. methylsulfonyl, trifluoromethyl and alkylthio e.g. methylthio. Where $R^1$ represents a substituted phenyl group the substituent or one of the substituents may, for example, be present in the para position.

The substituent $R^2$ may for example represent a hydrogen atom, a $C_{1-6}$ alkyl conveniently $C_{1-4}$ alkyl group e.g. methyl, an aryl e.g. phenyl group or the group $—COR^{1a}$ in which $R^{1a}$ represents an optionally substituted phenyl group e.g. unsubstituted phenyl. The preferred meanings for $R^2$ are methyl, or more particularly, hydrogen.

X preferably represents a halogen atom, especially a bromine atom or, more particularly, chlorine.

Especially preferred compounds of the present invention by virtue of their especially favourable metaphase arresting ability are:
(1) 5-chloro-1-(4-methylphenacyl)pyrimidin-2-one,
(2) 5-chloro-1-(4-nitrophenacyl)pyrimidin-2-one,
(3) 5-chloro-1-(2,4-dimethylphenacyl)pyrimidin-2-one,
(4) 5-chloro-1-(1-oxo-1-phenylprop-2-yl)pyrimidin-2-one,
(5) 5-chloro-1-(4-trifluoromethylphenacyl)pyrimidin-2-one,
(6) 5-chloro-1-(4-methylthiophenacyl)pyrimidin-2-one,
(7) 5-chloro-1-(4-chlorophenacyl)pyrimidin-2-one,
(8) 5-chloro-1-(4-fluorophenacyl)pyrimidin-2-one,
(9) 5-chloro-1-(4-hydroxyphenacyl)pyrimidin-2-one,
(10) 5-chloro-1-(3-methoxyphenacyl)pyrimidin-2-one,
(11) ethyl[4-(5-chloro-2-oxopyrimidin-1-yl)acetyl]-benzoate and
(12) 5-chloro-1-(4-cyanophenacyl)pyrimidin-2-one of which compounds 1, 2 and 7 are particularly preferred.

Salts of compounds of formula I may include, for example, salts with alkali metals or alkaline earth metals e.g. sodium, potassium, magnesium or calcium, or ammonium (including substituted ammonium) salts. Compounds according to the invention carrying hydroxy or amino groups may also in general, possess enhanced water-solubility, the latter, of course, forming acid addition salts for example with mineral acids such as e.g. hydrochloric or sulphuric acid or organic acids such as e.g. acetic, tartaric or citric acid.

It will be appreciated that the compounds according to the invention, depending on the groups present, may exist in optical forms and all such forms as well as mixtures thereof are included within the scope of the invention.

It will be further appreciated that, for pharmaceutical use, the salts referred to above will be physiologically compatible but other salts may find use, for example in the preparation of compounds of general formula I and their physiologically compatible salts.

The compounds of the invention are structurally quite simple and may be prepared by a variety of different processes. Reactions for the preparation of the six-membered pyrimidine ring system from ureas and three carbon atom components are well known in the art.

According to another aspect of the invention, therefore, we provide a process for the preparation of a compound of formula I as defined above wherein:
(a) A compound of the formula,

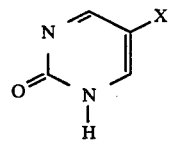

(wherein X, is as hereinbefore defined) or a salt thereof is reacted with an agent or agents serving to introduce the group

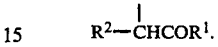

This agent may, for example, be a compound of formula:

$$R^2—CHY—COR^1 \quad \text{III}$$

(wherein $R^1$ and $R^2$ are as hereinbefore defined, Y represents a leaving atom or group e.g. a halogen atom, a hydroxy group or a reactive ether or ester derivative).

A compound of formula III is advantageously used in which Y represents an iodine, bromine or chlorine atom or a hydrocarbonsulphonyloxy derivative such as a mesylate, brosylate or tosylate.

The reaction between the compounds of formula II and III is conveniently effected in the presence of a polar solvent such as an alkanol e.g. ethanol or dimethylformamide or a halogenated hydrocarbon such as dichloromethane. The reaction may also conveniently be effected in the presence of a base, e.g. a tertiary organic base such as triethylamine or an inorganic base e.g. an alkali metal hydroxide, such as potassium hydroxide, or an alkali metal carbonate, such as sodium carbonate, in the presence of a phase transfer catalyst such as benzyltrimethylammonium chloride. Where a salt of the compound of formula (II) is used, an added base will not normally be required. Such a salt may, for example, be an alkali metal, e.g. sodium or potassium, salt.

The group of formula

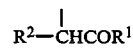

may also be introduced by a two stage reaction in which the compound of formula (II) is reacted with an O-silylating agent to form an O-silyl derivative, e.g. a trialkylsilyl ether, followed by reaction with a compound of formula (III), preferably in the presence of a Lewis acid.

The reagent serving to introduce the group

may, as indicated above, also be an alcohol of the formula $R^2CHOHCOR^1$. In this case the reaction is carried out in the presence of a condensing agent such as an acetal of a $C_{1-5}$ dialkylformamide e.g. dimethyl formamide. The alkyl groups of the acetal are preferably neopentyl groups, thus dimethylformamide dineopentylacetal is a preferred condensing agent.

Alternatively, the compound of formula III may be in the form of an acetal of a $C_{1-5}$ dialkylformamide carrying at least one acetal group derived from the alcohol $R^2CHOHCOR^1$.

(b) Deprotection of the protected keto group of a compound of the formula:

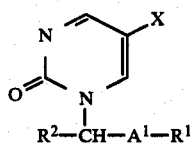
VII (wherein $R^1$, $R^2$ and X are as hereinbefore defined and $A^1$ represents a protected keto group). Deprotection may be effected according to conventional methods, for example by hydrolysis, e.g. basic hydrolysis using bases such as alkali metal hydroxides e.g. sodium or potassium hydroxide.

A compound of formula VII is preferably used in which the protected carbonyl group $A^1$ and/or a protected carbonyl group in $R^2$, where present, is in the form of a ketal group for example a ketal group derived from an alkanol, e.g. with 1 to 6 carbon atoms, such as methanol or ethanol or a 1,2-diol.

The compound of formula VII may be prepared by process (a) described above and process (e) described below.

(c) Oxidation of a compound of the formula:

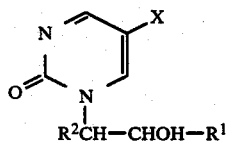
VIII (wherein $R^1$, $R^2$ and X are as hereinbefore defined).

The oxidation reaction may be effected using a reagent capable of oxidising a secondary hydroxyl group to a keto group, e.g. a chromium trioxide/pyridine.

The compound of formula VIII may be prepared by any convenient method, for example by process (a) above or process (e) hereinafter, followed where required by deprotection of a protected hydroxymethylene group.

(d) A compound of formula I in which X is hydrogen may be converted into a compound in which X is halogen by electrophilic halogenation e.g. using molecular chlorine or bromine.

(e) Starting materials for the processes (b) and (c) above may be prepared as follows:
a compound of the formula:

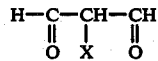
IV (wherein X is as hereinbefore defined) or a functional derivative thereof such as an enol, acetal, enol ether, enol thioether, imine or enamine derivative, is reacted with a reagent serving to replace the oxo groups or functionally equivalent groups in formula IV by a urea moiety

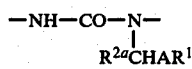

(wherein A represents a protected carbonyl, hydroxymethylene or protected hydroxymethylene group, $R^1$ is as hereinbefore defined, and $R^{2a}$ is as defined as above for $R^2$ except that a group of the formula $AR^{1a}$, where $R^{1a}$ has the above meaning, replaces the group $COR^1$).

The group A in the reagent serving to replace the oxo groups by a urea moiety preferably represents a protected carbonyl group or a hydroxymethylene or protected hydroxymethylene group, in which case the compound formed by reaction of the compound of formula IV with the said reagent is further reacted, either to remove the carbonyl protecting group or the oxidise the —CHOH— group, (if necessary after removing the hydroxyl protecting group) whereby a compound of formula I is formed. The removal of the carbonyl or hydroxyl protecting groups or the oxidation of the hydroxymethylene group may, for example, be effected as described under process (b) and (c) hereinafter.

In one variation, the compound of formula IV is reacted with a urea derivative of the formula,

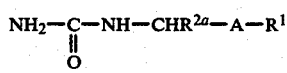
V (wherein A, $R^1$ and $R^{2a}$ are as hereinbefore defined).

The reaction of the compounds of formula IV and V may conveniently be effected under acid conditions, preferably in a solvent such as, for example, an alcohol, e.g. ethanol. The reaction conveniently proceeds at room temperature.

The urea reagent of formula V may, if desired, be replaced by a cyanamide of formula

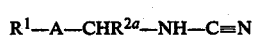

(wherein A, $R^1$ and $R^{2a}$ are as hereinbefore defined) which reacts to form an intermediate of formula

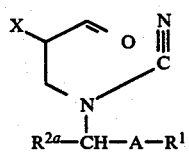
VI (wherein A, $R^1$, $R^{2a}$ and X are as hereinbefore defined) which may readily be cyclised, for example, in the presence of water.

A wide variety of reactions may be effected in order to convert one compound of formula I into another. Thus, for example, a compound of formula I in which $R^1$ represents or contains an ether and/or ester substituent may be converted into a corresponding compound of formula I in which the ether and/or ester substituent is replaced by a hydroxyl and/or carboxylic acid grouping respectively. Similarly a compound of formula I (in which $R^1$ represents a phenyl group substituted by both a benzyloxy group and by a benzyloxycarbonyl group) may be converted into a corresponding compound of formula I (in which $R^1$ represents a phenyl group substituted by both a carboxy group and by a hydroxy group)

by conventional methods e.g. by treatment with hydrogen bromide in acetic acid.

Certain compounds of formula I may exist in salt form. Where acidic groupings are present in the compounds of formula I salts may be formed with alkali metal or alkaline earth metals e.g. sodium, potassium, magnesium or calcium or ammonium (including substituted ammonium) salts. Such salts may be formed in the conventional manner e.g. by reaction with sodium or potassium hydroxide. Compounds of formula I carrying amino groups may form acid addition salts e.g. with mineral acid such as hydrochloric acid or sulphuric acid or organic acids such as acetic, tartaric or citric acid. Salts of the compounds of formula I may be converted to compounds of formula I per se by conventional techniques e.g. ion exchange.

According to a yet further feature of the present invention there are provided pharmaceutical compositions comprising as active ingredient, at least one compound of formula I as hereinbefore defined or, where an acidic or basic group is present, a physiologically compatible salt thereof in association with a pharmaceutical carrier or excipient.

For pharmaceutical administration the compounds of general formula I and their physiologically compatible salts may be incorporated into the conventional preparations in either solid or liquid form.

The compositions may, for example, be presented in a form suitable for rectal, parenteral or topical administration. Preferred forms include, for example suspensions, suppositories, creams, ointments and lotions and solutions e.g. for injection or infusion or for ingestion by the gastro-intestinal tract. Solutions for injection are especially preferred.

The active ingredient may be incorporated in excipients customarily employed in pharmaceutical compositions such as, for example, cocoa butter, aqueous or non-aqueous vehicles, fatty substances of animal or vegetable origin, paraffin derivatives glycols, various wetting, dispersing or emulsifying agents and/or preservatives.

Advantageously the compositions may be formulated as dosage units, each unit being adapted to supply a fixed dose of active ingredient. Suitable dosage units for adults contain from 50 mg to 1.0 g of active ingredient.

Thus according to a further feature of the present invention there is provided a method of combating or a method for the prophylaxis of abnormal cell proliferation in a host which comprises administering to said host an effective amount of a compound of formula I as hereinbefore defined or where an acidic or basic group is present, a physiologically compatible salt thereof. The dosage, which may be varied according to the compound used, the subject treated and the complaint concerned, may, for example, be from 0.25 to 7.0 g in a day in adults.

It will normally be necessary to have a knowledge of cell cycle kinetics (for example as determined by cytofluorometry) of both the normal and abnormal cells and to prepare time schedules which indicate how long after administration of the drug the majority of the abnormal cells will reach a phase which is susceptible to attack by a chosen cytotoxic drug while the majority of normal cells are in a non-susceptible phase. These periods will naturally differ wildly. Suitable cytotoxic drugs include cytosine arabinoside and hydroxyurea which are cytotoxic against cells in the S-phase. Since the S-phase is generally longer than the other phases, it is easier to find appropriate time schedules when using cytotoxic drugs active in this phase.

The following Examples are given by way of illustration only:

EXAMPLE 1

5-Chloro-1-phenacylpyrimidin-2-one

A solution of 5-chloropyrimidin-2-one (293 mg) and α-bromoacetophenone (616 mg) in triethylamine (0.6 ml) and ethanol (40 ml) was stirred at ambient temperature for two hours. After evaporation of solvents, the residue was triturated with water to give the title products (516 mg). This was combined with similar material (59 mg) from another reaction and crystallised from ethanol to give the title pyrimidinone: yield (364 mg): m.p. 209°–212° dec: $\lambda_{max}^{EtOH}$ 244 nm ($\epsilon$ 16850), 288 nm ($\epsilon$ 1870), 333.5 nm ($\epsilon$ 3950), $\lambda_{inf}$ 238 nm ($\epsilon$ 16280).

EXAMPLE 2

5-Bromo-1-phenacylpyrimidin-2-one

A solution of 5-bromopyrimidin-2-one hydrobromide (512 mg) and α-bromoacetophenone (398 mg) in triethylamine (2 ml) and ethanol (10 ml) was stirred at ambient temperature for three and a half hours. After evaporation of solvents, the residue was triturated with water. The product was filtered off and recrystallised from ethanol to give the title pyrimidinone: yield 253 mg: m.p. 161°–163°, $\lambda_{max}^{EtOH}$ 241.5 nm ($\epsilon$ 18810), 285 nm ($\epsilon$ 1690), 334.5 nm ($\epsilon$ 3190).

EXAMPLE 3

5-Iodo-1-phenacylpyrimidin-2-one

A suspension of 5-iodopyrimidin-2-one (556 mg) and α-bromoacetophenone (533 mg) in triethylamine (0.5 ml) and ethanol (50 ml) was stirred at ambient temperature for 7½ hours. The resulting solution was evaporated and the residue triturated with water. This product was purified by preparative thin-layer chromatography on silica before crystallisation from ethyl acetate to give the title pyrimidinone: yield 253 mg: m.p. 155°–157°: $\lambda_{max}^{EtOH}$ 238.5 nm ($\epsilon$ 23070), 340 nm ($\epsilon$ 2400), $\lambda_{inf}$ 250 nm ($\epsilon$ 17160), 275 nm ($\epsilon$ 1780).

EXAMPLE 4

1-(4-Bromophenacyl)-5-chloropyrimidin-2-one

A suspension of 5-chloropyrimidin-2-one hydrochloride (167 mg), 4-bromophenacylbromide (278 mg) in triethylamine (1 ml) and ethanol (5 ml) was stirred at ambient temperature for three quarters of an hour. After evaporation of solvents the residue was triturated with water to give a solid (269 mg). This was combined with similar material (271 mg) from another reaction and crystallised from ethanol to give the title pyrimidinone: 262 mg m.p. 225°–232°: $\lambda_{max}^{EtOH}$ 256 nm ($\epsilon$ 21210), 332 nm ($\epsilon$ 2290).

EXAMPLE 5

5-Chloro-1-(4-methylphenacyl)pyrimidin-2-one

A suspension of 5-chloropyrimidin-2-one hydrochloride (501 mg) and 2-bromo-4-methylacetophenone (638 mg) in triethylamine (1 ml) and ethanol (20 ml) was stirred at ambient temperature for one and three quarter hours, then cooled and the solid filtered off. The filtrate was evaporated, the residue was diluted with water (100 ml) and the product was extracted with ethyl acetate (3×50 ml). This was combined with the solid and crystallised from acetone: yield 306 mg, m.p. 214°–217° dec: $\lambda_{max}^{EtOH}$ 253 nm ($\epsilon$ 19760), 332 nm ($\epsilon$ 2620), $\lambda_{inf}$ 232 nm ($\epsilon$ 11040).

EXAMPLE 6

Methyl 5-(5-chloro-2-oxopyrimidin-1-yl)acetylsalicylate

A solution of 5-chloropyrimidin-2-one hydrochloride (508 mg) and methyl 5-bromoacetylsalicylate (827 mg) in triethylamine (1 ml) and ethanol (20 ml) was stirred at ambient temperature for 1¾ hours, by which time a precipitate had formed. This suspension was chilled in ice, and the collected solid was crystallised from chloroform-ethanol to give the title pyrimidinone: yield 442 mg: m.p. 203°–204° dec: $\lambda_{max}^{EtOH}$ 228.5 nm ($\epsilon$ 40720), 269.5 nm ($\epsilon$ 16930), 312.5 nm ($\epsilon$ 6320).

EXAMPLE 7

5-Chloro-1-(4-methoxyphenacyl)pyrimidin-2-one

A suspension of 5-chloropyrimidin-2-one hydrochloride (502 mg), α-bromo-4-methoxyacetophenone (687 mg), triethylamine (1 ml) and ethanol (20 ml) was stirred at ambient temperature for 2 hours, during which the suspension formed a solution from which a solid crystallised out. The solid was crystallised from acetone to give the title pyrimidinone: yield. 449 mg; m.p. 212°–214° C.: $\lambda_{max}^{EtOH}$ 222.5 nm ($\epsilon$ 19850), 277 nm ($\epsilon$ 18000), 330 nm ($\epsilon$ 3725).

EXAMPLE 8

5-Fluoro-1-phenacylpyrimidin-2-one

A solution of 5-fluoropyrimidin-2-one (480 mg) and α-bromoacetophenone (843 mg) in triethylamine (1 ml) and ethanol (20 ml) was stirred at ambient temperature for 3½ hours. The resulting suspension was chilled in ice. The solid was collected by filtration, then crystallised twice from ethanol to give the title pyrimidinone (206 mg yield); m.p. 167°–175°, $\lambda_{max}^{EtOH}$ 243 nm ($\epsilon$ 15110), 331 nm ($\epsilon$ 3590), $\lambda_{inf}$ 283 nm ($\epsilon$ 1870), 290 nm ($\epsilon$ 1890), 344 nm ($\epsilon$ 2740).

EXAMPLE 9

5-Chloro-1-(3,4-dihydroxyphenacyl)pyrimidin-2-one (a) α-Chloro-3',4'-diphenylmethylenedioxy acetophenone A suspension of α-chloro-3'4'-dihydroxyacetophenone (4.65 g) in dichlorodiphenylmethane (5 ml) was stirred and heated at ca 180°, giving a brown solution. After 5 mins the solution was cooled, diluted with chloroform and evaporated to a viscous oil (10.5 g). A portion of this was triturated with diethyl ether, giving a solid (1.04 g). This was crystallised from di-isopropyl ether to give the title acetophenone (0.74 g), m.p. 75°–79°, $\lambda_{max}^{EtOH}$ 232 nm ($\epsilon$ 22180), 277.5 nm ($\epsilon$ 7330), 312 nm ($\epsilon$ 9210).

(b) 5-Chloro-1-(3,4,-diphenylmethylenedioxyphenacyl)-pyrimidin-2-one

A solution of 5-chloropyrimidin-2-one hydrochloride (538 mg) and α-chloro-3',4'-diphenylmethylenedioxyacetophenone (1.009 g) in triethylamine (1 ml) and ethanol (20 ml) was stirred at ambient temperature for 19 hours. The resulting suspension was chilled in ice, and the collected solid was crystallised from chloroform to give the solvated title pyrimidinone: yield 334 mg; m.p. 269°–271° dec: $\lambda_{max}^{EtOH}$ 229 nm, ($\epsilon$ 28850), 276 nm ($\epsilon$ 7060) 312.5 nm ($\epsilon$ 9170).

(c) 5-Chloro-1-(3,4-dihydroxyphenacyl)pyrimidin-2-one

A solution of 5-chloro-1(3,4-diphenylmethylenedioxyphenacyl)pyrimidin-2-one (1.595 g) in trifluoroacetic acid (15 ml) was stirred at ambient temperature for 2½ hours. After evaporation of solvent, the residue was triturated with diethyl ether to give a solid. This was crystallised from ethanol to give the title pyrimidinone (662 mg yield), m.p. gradual darkening above 250°, melted 265°–270° (dec): $\lambda_{max}^{EtOH}$ 230 nm ($\epsilon$ 21930), 281 nm ($\epsilon$ 9410), 322 nm ($\epsilon$ 11130).

EXAMPLE 10

5-Chloro-1-(4-nitrophenacyl)pyrimidin-2-one

A mixture of 5-chloropyrimidin-2-one (787 mg) and 2-bromo-4'-nitroacetophenone (1.47 g) in triethylamine (2 ml) and ethanol (40 ml) was stirred at ambient temperature for 1 hr. The reaction mixture was diluted with water and the solid filtered off.

Crystallisation of the solid from acetone gave the title compound (942 mg) m.p. 232°–236°: $\lambda_{max}^{EtOH}$ 258 nm ($\epsilon$ 16340), $\lambda_{inf}$ 305 nm ($\epsilon$ 2820), 312 ($\epsilon$ 2570), 330 nm ($\epsilon$ 2160).

EXAMPLE 11

5-Chloro-1-(2,4-dimethylphenacyl)pyrimidin-2-one

A mixture of 5-chloropyrimidin-2-one (425 mg) and 2-bromo-2',4'-dimethylacetophenone (682 mg) in triethylamine (1 ml) and ethanol (20 ml) was stirred at ambient temperature for 2 hours. The reaction mixture was diluted with water and the solid filtered off.

Crystallisation of the solid from acetone gave the title compound (579 mg) m.p. 221°–222°. $\lambda_{max}^{EtOH}$ 253.5 nm ($\epsilon$ 15880), 293 nm ($\epsilon$ 2370), 334 nm ($\epsilon$ 3210), $\lambda_{inf}$ 227 nm ($\epsilon$ 12370).

EXAMPLE 12

5-Chloro-1-(1-oxo-1-phenylprop-2-yl)pyrimidin-2-one

A solution of 5-chloropyrimidin-2-one (394 mg) and α-bromopropiophenone (0.5 ml) in triethylamine (1 ml) and ethanol (20 ml) was stirred at ambient temperature for 2.75 hours. The solution was evaporated and the residue was triturated with water (50 ml) giving an oily solid. This was extracted with ethyl acetate (3×50 ml). The combined extracts were washed with brine (50 ml), dried (MgSO$_4$) and evaporated to a gum. This was crystallised from acetone-petrol (b.p. 40°–60°) to give the title pyrimidinone (306 mg,); m.p. 125°–127°; $\lambda_{max}^{EtOH}$ 232 nm ($\epsilon$ 15400), 245 nm ($\epsilon$ 15480), 335 nm ($\epsilon$ 3970).

EXAMPLE 13

5-Chloro-1-dibenzoylmethyl-pyrimidin-2-one

A solution of 5-chloropyrimidin-2-one (404 mg) and α-bromo-dibenzoyl methane (923 mg) in triethylamine (1 ml) and ethanol (20 ml) was chilled in ice and stirred for one hour. After evaporation of solvents, the residue was purified by preparative thin-layer chromatography on silica developed with chloroform. The resulting material was crystallised twice from acetone to give the title pyrimidinone (457 mg,); m.p. 220°–223°; $\lambda_{max}^{EtOH}$ 226 nm ($\epsilon$ 20820), 326 nm ($\epsilon$ 10630), $\lambda_{inf}$ 244 nm ($\epsilon$ 15360).

EXAMPLE 14

5-Chloro-1-(4-trifluoromethylphenacyl)pyrimidin-2-one

A suspension of 5-chloropyrimidin-2-one (408 mg). and 2-bromo-4'-trifluoromethyl-acetophenone (824 mg) in triethylamine (1 ml) and ethanol (20 ml) was stirred at ambient temperature for 45 mins. Water (100 ml) was added and the precipitate was collected. This solid was crystallised from acetone to give the title pyrimidinone (571 mg,); m.p. 243°–245°; $\lambda_{max}^{EtOH}$ 235.5 nm ($\epsilon$ 20040), 282 nm ($\epsilon$ 1880), 333.5 nm ($\epsilon$ 1860), $\lambda_{inf}$ 287.5 nm ($\epsilon$ 1790).

EXAMPLE 15

5-Chloro-1-(4-methylthiophenacyl)pyrimidin-2-one

A suspension of 5-chloropyrimidin-2-one (312 mg) and 2-bromo-4'-methylthioacetophenone (525 mg) in triethylamine (1 ml) and ethanol (20 ml) was stirred at ambient temperature for 2.25 hours. The resulting suspension was concentrated at reduced pressure then diluted with water (50 ml). The collected precipitate was crystallised from acetone to give the title pyrimidinone (404 mg,); m.p. 192°–197°, $\lambda_{max}^{EtOH}$ 229 nm ($\epsilon$ 14450), 312 nm ($\epsilon$ 21470), $\lambda_{inf}$ 239.5 nm ($\epsilon$ 9930).

EXAMPLE 16

5-Chloro-1-(4-methylsulphonylphenacyl)pyrimidin-2-one

A suspension of 5-chloropyrimidin-2-one (411 mg) and 2-bromo-4'-methylsulphonyl acetophenone (835 mg) in triethylamine (1 ml) and ethanol (20 ml) was stirred at ambient temperature for one hour. The resulting suspension was concentrated at reduced pressure then diluted with water (100 ml). The collected precipitate was crystallised from acetone, then from ethanol to give the title pyrimidinone (235 mg); m.p. 257°–258°; $\lambda_{max}^{EtOH}$ 242 nm ($\epsilon$ 23650), 286 nm ($\epsilon$ 1950), 334 nm ($\epsilon$ 1680), $\lambda_{inf}$ 293 nm ($\epsilon$ 1850).

EXAMPLE 17

5-Chloro-1-(4-chlorophenacyl)primidin-2-one

A suspension of 5-chloropyrimidin-2-one (1.202 g) and 2-bromo-4'-chloroacetophenone (2.114 g) in triethylamine (2 ml) and ethanol (20 ml) was stirred at ambient temperature for 75 mins. The resulting suspension was filtered, the solid was washed with water then crystallised from acetone to give the title pyrimidinone (1.973 g,); m.p. 216°–218°; $\lambda_{max}^{EtOH}$ 252 nm ($\epsilon$ 22360), 233 nm ($\epsilon$ 2080), $\lambda_{inf}$ 288 nm ($\epsilon$ 1530).

EXAMPLE 18

5-Chloro-1-(4-methylsulphinylphenacyl)pyrimidin-2-one

A suspension of 5-chloropyrimidin-2-one (399 mg). and 2-bromo-4'-methylsulphinylacetophenone (784 mg) in triethylamine (1 ml) and ethanol (20 ml) was stirred at ambient temperature for one hour, when the resulting suspension was chilled in ice. The collected solid was crystallised from ethanol to give the title pyrimidinone (509 mg,); m.p. 219°–220°; $\lambda_{max}^{EtOH}$ 233.5 nm ($\epsilon$ 17920), 332 nm ($\epsilon$ 2060), $\lambda_{inf}$ 266 nm ($\epsilon$ 9280).

EXAMPLE 19

5-Chloro-1-(4-fluorophenacyl)pyrimidin-2-one

A solution of 5-chloropyrimidin-2-one (1.309 g) and 2-chloro-4'-fluoroacetophenone (1.726 g) in triethylamine (2 ml) and ethanol (50 ml) was stirred and heated at reflux for 1½ hours. After evaporation of solvents, the residue was triturated with water (100 ml). The resulting collected solid was crystallised from ethanol then acetone, but still required purification, by preparative thin-layer chromatography on silica developed in chloroform-ethanol (25:1 v/v), before crystallisation from propan-2-ol to give the title pyrimidinone (204 mg,); 196°–202°; $\lambda_{max}^{EtOH}$ 245 nm ($\epsilon$ 17780), 333 nm ($\epsilon$ 2090), $\lambda_{inf}$ 236 nm ($\epsilon$ 15230), 280 nm ($\epsilon$ 980).

EXAMPLE 20

5-Chloro-1-(4-hydroxyphenacyl)pyrimidin-2-one

A suspension of 5-chloropyrimidin-2-one (405 mg) and 2-bromo-4'-hydroxyacetophenone (646 mg) in triethylamine (1 ml) and ethanol (20 ml) was stirred at ambient temperature, giving a clear solution. A precipitate had formed after an hour. After 23½ hours, 2N-hydrochloric acid (5 ml) was added to the suspension and the solid was collected. This was washed with ethanol to give the title pyrimidinone (679 mg,); m.p. 260° with decomposition; $\lambda_{max}^{EtOH}$ 224 nm ($\epsilon$ 17300), 282.5 nm ($\epsilon$ 15660), 353 nm ($\epsilon$ 4900).

EXAMPLE 21

5-Chloro-1-(2-methoxyphenacyl)pyrimidin-2-one

A solution of 5-chloropyrimidin-2-one (541 mg) and 2-bromo-2'-methoxyacetophenone (954 mg) in triethylamine (1 ml) and ethanol (25 ml) was stirred at ambient temperature for 3½ hours. After evaporation of solvents, the residue was dissolved in ethyl acetate (150 ml) and this solution was washed with water (50 ml) and brine (25 ml), dried (MgSO$_4$) and evaporated to give a foam. This was purified by preparative thin-layer chromatography on silica, developed in chloroform, then chloroform-ethanol (25:1) before crystallisation from ethyl acetate to give the title pyrimidinone (347 mg,); m.p. 123°–125°; $\lambda_{max}$ 248.5 nm $\epsilon$ 12200), 317.5 nm ($\epsilon$ 6700), $\lambda_{inf}$ 229.5 nm ($\epsilon$ 12440), 349 nm ($\epsilon$ 2640).

EXAMPLE 22

5-Chloro-1-(3-methoxyphenacyl)pyrimidin-2-one

A solution of 5-chloropyrimidin-2-one (504 mg) and 2-bromo-3'-methoxyacetophenone (880 mg) in triethylamine (1 ml) and ethanol (50 ml) was stirred at ambient temperature for 20 hours. After evaporation of solvents, the residue was triturated with water (50 ml). The resulting solid was crystallised from ethyl acetate to give the title pyrimidinone (220 mg,); m.p. 134°–137°; $\lambda_{max}^{EtOH}$ 249.5 nm ($\epsilon$ 12660), 317 nm ($\epsilon$ 4070), $\lambda_{inf}$ 334.5 nm ($\epsilon$ 2950), 344.5 nm ($\epsilon$ 1990).

EXAMPLE 23

1-(4-Benzamidophenacyl)-5-chloropyrimidin-2-one (a) 4'-Benzamido-2-bromoacetophenone A warm solution of 4'-benzamidoacetophenone (1.031 g) in chloroform (100 ml) was treated with bromine (0.22 ml). After dilution with more chloroform (50 ml), the resulting solution was washed with 2N-sodium hydroxide solution (2×25 ml) and water (50 ml), dried (MgSO$_4$) and evaporated to a white solid (1.315 g). This was crystallised from ethanol to give the title acetophenone (922 mg); m.p. 171°-174°.

(b) 1-(4-Benzamidophenacyl)-5-chloropyrimidin-2-one

A suspension of 5-chloropyrimidin-2-one (338 mg) and 4'-benzamido-2-bromoacetophenone (766 mg) in triethylamine (1 ml) and dimethylformamide (10 ml) was stirred at ambient temperature, giving a solution, quickly followed by formation of a precipitate. After 45 mins, water (100 ml) was added to the suspension. The collected solid was crystallised from glacial acetic acid to give the title pyrimidinone (439 mg,); m.p. 290°-303°; $\lambda_{max}^{EtOH}$ 226 nm ($\epsilon$ 16230), 302.5 nm ($\epsilon$ 20370).

EXAMPLE 24

Ethyl[4-(5-chloro-2-oxopyrimidin-1-yl)acetyl]benzoate (a) Ethyl (4-bromoacetyl)benzoate A solution of ethyl 4-acetylbenzoate (1.586 g) in chloroform (50 ml) was stirred at ambient temperature and treated with bromine (0.43 ml). After two hours the resulting solution was evaporated to a solid, which was crystallised from ethanol to give the title benzoate (960 mg); m.p. 73°-75°.

(b) Ethyl [4-(5-chloro-2-oxopyrimidin-1-yl)acetyl]benzoate

A suspension of 5-chloropyrimidin-2-one (401 mg) and ethyl 4-bromoacetylbenzoate (812 mg) in triethylamine (1 ml) and ethanol (20 ml) was stirred at ambient temperature for one hour. Water (100 ml) was added and the collected solid was crystallised from ethanol to give the title pyrimidinone (500 mg,); m.p. 215°-216°; $\lambda_{max}^{EtOH}$ 250.5 nm ($\epsilon$ 24130), $\lambda_{inf}$ 237 nm ($\epsilon$ 16520), 304.5 nm ($\epsilon$ 3050).

EXAMPLE 25

5-Chloro-1-(4-cyanophenacyl)pyrimidin-2-one

A suspension of 5-chloropyrimidin-2-one (412 mg) and 2-bromo-4'-cyanoacetophenone (677 mg) in triethylamine (1 ml) and ethanol (20 ml) was stirred at ambient temperature for one hour. Water (100 ml) was added and the collected solid was crystallised from ethyl acetate to give the title pyrimidinone (375 mg,); m.p. 236°-240°; $\lambda_{max}^{EtOH}$ 248 nm ($\epsilon$ 26140), 289 nm ($\epsilon$ 2130), $\lambda_{inf}$ 254 ($\epsilon$ 22800).

EXAMPLE 26

5-Chloro-1-desylpyrimidin-2-one

A solution of 5-chloropyrimidin-2-one (406 mg) and desyl chloride (2-chloro-2-phenyl acetophenone) (692 mg) in triethylamine (1 ml) and ethanol (20 ml) was stirred at ambient temperature for one hour, then heated at reflux for 1½ hours. After evaporation of solvents, the residue was dissolved in ethyl acetate (150 ml). The solution was washed with water (100 ml), dried (MgSO₄) and evaporated to a foam which was crystallised from ethyl acetate to give the title pyrimidinone (393 mg,); m.p. 145°-146°; $\lambda_{max}^{EtOH}$ 230 nm ($\epsilon$ 15960), 250 nm ($\epsilon$ 15000), 335 nm ($\epsilon$ 4700), $\lambda_{inf}$ 262.5 nm ($\epsilon$ 8400), 269 n, ($\epsilon$ 4420).

EXAMPLE 27

5-Chloro-1-phenacylpyrimidin-2-one

A solution of 5-chloro-1-(2-hydroxyphenethyl)-pyrimidin-2-one (251 mg) in pyridine (6 ml) was added to the stirred suspension obtained by adding chromium trioxide (408 mg) to pyridine (4 ml). After 2½ hours the mixture was diluted with water (10 ml) and the products were extracted with ethyl acetate (150 ml). The extract was washed with N-hydrochloric acid (2×25 ml) and water (50 ml), dried (MgSO₄) and evaporated to a solid (271 mg). Crystallisation of this from ethanol followed by purification of the mother liquor material by preparative-layer chromatography gave the title pyrimidinone (48 mg), whose p.m.r. spectrum (in deuteriodimethylsulphoxide) and t.l.c. characteristics were identical to those of authentic material (vide supra).

PHARMACEUTICAL COMPOSITION EXAMPLES

Example A

Injection solution

1. Active ingredient: 50 mg
2. Polysorbate 80: 2.50 mg
3. Sodium chloride: 45 mg
4. Water for injection: to 5.0 ml The sterile active ingredient, precipitated as a very fine powder, is dispersed aseptically in an aqueous vehicle containing the wetting agent (Polysorbate 80) and sufficient sodium chloride to produce an approximately isotonic solution thus providing a suspension which may be used for deep intramuscular injection. Buffer salts may be incorporated (with a consequent reduction in the quantity of sodium chloride) to provide a suspension at the appropriate pH to ensure optimum stability of the compound before injection. The product may be presented as a dry filled vial of active ingredient together with a sterile ampoule of the remaining ingredients to permit extemporaneous preparation of the suspension immediately before injection.

EXAMPLE B

Injection solution

1. Active ingredient: 100 mg
2. Aluminium monostearate: 5 mg
3. Fractionated coconut oil to: 1 ml Sterile active ingredient in the form of a very fine powder is dispersed aseptically in a sterile oily vehicle containing a suspending agent whose structure is built up during the heat sterilisation of the vehicle. Such a product may be presented as a pre-prepared suspension for intramuscular injection. The dose administered may be adjusted by alteration of the dose volume. The product may be presented in multidose vials, sealed with oil resistant rubber plugs to permit withdrawal of the required dose volume.

We claim:

1. Compounds of the general formula

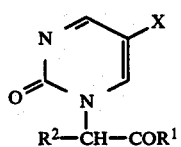

I wherein
X represents a halogen atom or a trifluoromethyl group;
R¹ represents a C₆₋₁₀ carbocyclic aromatic group optionally substituted by one or two substituents selected from halogen atoms, hydroxyl, alkoxy having from 1 to 6 carbon atoms, aralkoxy having from 7 to 10 carbon atoms, amino, amino substituted with one or two alkyl groups having from 1–6 carbon atoms, aralkyl groups having from 7–10 carbon atoms, phenyl groups, alkanoyl groups in which the alkyl moiety has from 1–6 carbon atoms, haloalkanoyl groups in which the alkyl moiety has from 1–6 carbon atoms or benzoyl groups, cyclic imido groups derived from dibasic alkanoic acids having from 1–6 carbon atoms in the alkyl moiety, from aralkanoic acids having from 7–10 carbon atoms in the aralkyl moiety or from benzene dicarboxylic acids, —S(O)$_n$R$^a$ (in which n is 0, 1 or 2 and R$^a$ is lower alkyl), nitro, cyano, carboxyl, alkoxycarbonyl having 1–6 carbon atoms in the alkyl moiety, carboxamido, C$_{1-4}$ alkyl, phenyl and methylenedioxy groups, which methylenedioxy group may carry alkyl substituents or, a perfluorinated alkyl group; and R$^2$ represents a hydrogen atom or a lower alkyl C$_{7-16}$ aralkyl or C$_{6-10}$ aryl group or the group COR$^{1a}$ (in which R$^{1a}$ is as defined for R$^1$, R$^1$ and R$^{1a}$ being the same or different); and the physiologically compatible salts thereof.

2. Compounds as claimed in claim 1 wherein R$^1$ represents a phenyl group optionally substituted by one or two substituents selected from halogen atoms and C$_{1-4}$ alkyl, C$_{1-4}$ alkoxy, hydroxy, alkoxycarbonyl, nitro, trifluoromethyl, C$_{1-6}$ alkylthio, C$_{1-6}$ alkylsulphonyl, cyano, C$_{1-6}$ alkylsulphinyl and benzoylamino group.

3. Compounds as claimed in claim 2 wherein R$^1$ represents a phenyl group substituted by one or more substituents selected from halogen atoms and trifluoromethyl, methoxycarbonyl, ethoxycarbonyl, methoxy, methyl, benzoylamino, methylsulphinyl, methylsulphonyl and methylthio groups.

4. Compounds as claimed in claim 1 wherein R$^2$ represents a hydrogen atom, a methyl or phenyl group or a group of the formula —COR$^{1a}$ in which R$^{1a}$ represents an unsubstituted phenyl group.

5. Compounds as claimed in claim 4 wherein R$^2$ represents a hydrogen atom.

6. Compounds as claimed in claim 1 wherein X represents a halogen atom.

7. Compounds as claimed in claim 1 which are
5-chloro-1-(2,4-dimethylphenacyl)pyrimidin-2-one,
5-chloro-1-(1-oxo-1-phenylprop-2-yl)pyrimidin-2-one,
5-chloro-1-(4-trifluoromethylphenacyl)pyrimidin-2-one,
5-chloro-1-(4-methylthiophenacyl)pyrimidin-2-one,
5-chloro-1-(4-fluorophenacyl)pyrimidin-2-one,
5-chloro-1-(4-hydroxyphenacyl)pyrimidin-2-one,
5-chloro-1-(3-methoxyphenacyl)pyrimidin-2-one,
Ethyl[4-(5-chloro-2-oxopyrimidin-1-yl)acetyl]benzoate or
5-chloro-1-(4-cyanophenacyl)pyrimidin-2-one.

8. A compound as claimed in claim 1 which is 5-chloro-1-(4-nitrophenacyl)pyrimidin-2-one.

9. A compound as claimed in claim 1 which is 5-chloro-1-(4-chlorophenacyl)pyrimidin-2-one.

10. A compound as claimed in claim 1 which is 5-chloro-1-(4-methylphenacyl)pyrimidin-2-one.

11. Pharmaceutical compositions for use in combined therapy for combating abnormal cell proliferation comprising as active ingredient at least one compound of formula I as defined in claim 1 or a physiologically compatible salt thereof in association with a pharmaceutical carrier or excipient said active ingredient being present in an effective amount to achieve metaphase arrest.

12. In a method of combined therapy for combating abnormal cell proliferation in a host which comprises administering to said host an amount of a metaphase arrest agent sufficient to cause the division cycle of cells within said host to be arrested in the metaphase, the improvement comprising using as said metaphase arrest agent a compound of formula I as defined in claim 1 or a physiologically compatible salt thereof.

* * * * *